United States Patent [19]

Hagen et al.

[11] Patent Number: 5,235,115

[45] Date of Patent: Aug. 10, 1993

[54] PREPARATION OF 2-ALKOXY-6-ETHYLNAPHTHALENES

[75] Inventors: Gary P. Hagen, West Chicago; Wen-Dong Chang, Naperville; Andreas B. Ernst, Glen Ellyn; David A. Palmer, Naperville, all of Ill.; Daniel B. Pourreau, Downingtown, Pa.; Patrick E. McMahon, Wheaton; John G. Schaffhausen, Naperville, both of Ill.

[73] Assignee: Amoco Corporation, Chicago, Ill.

[21] Appl. No.: 745,482

[22] Filed: Aug. 15, 1991

Related U.S. Application Data

[63] Continuation-in-part of Ser. No. 568,581, Aug. 16, 1990, abandoned, which is a continuation-in-part of Ser. No. 544,272, Jun. 26, 1990.

[51] Int. Cl.$^5$ .................. C07C 41/20; C07C 41/22; C07C 41/18
[52] U.S. Cl. ................... 568/628; 568/632; 568/634
[58] Field of Search ............ 568/632, 634, 628; 570/196, 198; 585/612, 641

[56] References Cited

U.S. PATENT DOCUMENTS

| 2,388,758 | 11/1945 | Mills | 260/671 |
|---|---|---|---|
| 3,288,823 | 11/1966 | Vanderwerff | 570/196 |
| 3,651,148 | 3/1972 | Nelson | 568/634 |
| 4,045,501 | 8/1977 | Bianchi | 570/196 |
| 4,454,364 | 6/1984 | Farcasiu et al. | 585/470 |
| 4,873,386 | 10/1989 | Hagen et al. | 585/471 |
| 4,950,824 | 8/1990 | Shiroto et al. | 585/320 |

FOREIGN PATENT DOCUMENTS 0116353 10/1978 Japan .
0110632 6/1984 Japan .

*Primary Examiner*—Marianne M. Cintins
*Assistant Examiner*—Margaret J. Page
*Attorney, Agent, or Firm*—Thomas E. Nemo; Wallace L. Oliver; Frank J. Sroka

[57] ABSTRACT

A method for the selective ethylation of 2-alkoxy-naphthalene compounds at the 6 position of the naphthalene nucleus is disclosed.

18 Claims, No Drawings

PREPARATION OF 2-ALKOXY-6-ETHYLNAPHTHALENES

This application is a continuation-in-part of U.S. Ser. No. 568,581, filed Aug. 16, 1990, now abandoned; which is a continuation-in-part of U.S. Ser. No. 544,272 filed Jun. 26, 1990.

FIELD OF THE INVENTION

This invention concerns the highly selective production of 2-alkoxy-6-ethylnaphthalenes and 2-aryloxy-6-ethylnaphthalenes by the selective ethylation of a 2-alkoxy- or 2-aryloxynapthalene compound.

More particularly, this invention concerns the highly selective production of 2-methoxy-6-ethylnaphthalene by the selective ethylation of 2-methoxynaphthalene.

BACKGROUND OF THE INVENTION

2-Aryloxy- and 2-alkoxy-6-ethylnaphthalene compounds are useful as intermediates for the preparation of other organic compounds. For example, we have determined that 2-methoxy-6-ethylnaphthalene, a 2-alkoxy-6-ethylnaphthalene compound, is an intermediate suitable for the synthesis of (s)-6-methoxy-α-methyl-2-naphthaleneacetic acid, also known as d-2-(6-methoxy-2-naphthyl) propionic acid, and commonly referred to as Naproxen. Naproxen is an analgesic and anti-inflammatory agent. The structure of 2-(6-methoxy-2-naphthyl) propionic acid, i.e. the racemic compound, is as follows:

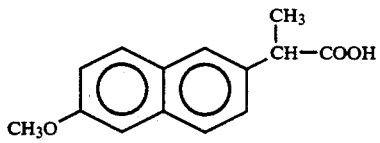

However, heretofore known methods for preparing 2-methoxy-6-ethylnaphthalene are complicated and, therefore, undesirable for large-scale manufacturing processes. For example, 2-methoxy-6-ethylnaphthalene has been prepared by acetylating 2-methoxynaphthalene in the usual Friedel-Crafts manner using a stoichiometric amount of Friedel-Crafts catalyst to form 2-methoxy-6-acetylnaphthalene. However, the yield of the 2,6-product was reported to be about 35 percent and it was difficult to separate the desired 2-methoxy-6-acetylnaphthalene from the 2-methoxy-1-acetylnaphthalene that was also produced in the reaction. Furthermore, in order to prepare 2-methoxy-6-ethylnaphthalene an additional step was required wherein the acetyl moiety on the 2-methoxy-6-acetynaphthalene molecule was reduced to an ethyl moiety using a Clemmensen reduction procedure.

The art therefore needs an improved method for the production of 2-aryloxy- or 2-alkoxynaphthalenes and, in particular, the art needs an improved method for the preparation of 2-methoxy-6-ethylnaphthalene. The present invention provides such an improved method. Also, although Naproxen contains a methoxy group, it is possible that the substitution of the methoxy group with an aryloxy or other alkoxy group may provide for compositions also having analgesic and/or anti-inflammatory activity. The present invention makes possible a simplified preparation of these compositions by making available the 2-aryloxy- and 2-alkoxy-6-ethylnaphthalene starting materials.

SUMMARY OF THE INVENTION

The present invention is a method for ethylating a 2-alkoxynaphthalene or a 2-aryloxynaphthalene as a feed compound, which comprises reacting the feed compound in the liquid phase with an ethylating agent comprising a triethylbenzene, a tetraethylbenzene, pentaethylbenzene, or a mixture thereof at a level of from about 0.5 to about 10 moles of the ethylating agent per mole of the feed, in the presence of a catalyst comprising a Lewis acid or a Bronsted acid alkylation catalyst or mixture thereof.

In the method of this invention an ethyl moiety is transferred from one or more polyethylbenzene ethylating agents to the 6 position of the 2-alkoxy- or 2-aryloxynaphthalene molecule, i.e. a transethylation occurs. Thus, the method of this invention provides for a simple, efficient and heretofore unknown method for preparing 2-aryloxy- or 2-alkoxy-6-ethylnaphthalenes.

DETAILED DESCRIPTION OF THE PREFERRED EMBODIMENTS

The feed compounds for the method of this invention are 2-alkoxynaphthalenes and 2-aryloxynaphthalenes. The hydrocarbyl portion of the alkoxy moiety of the 2-alkoxynaphthalene contains 1 to about 20 carbon atoms, and the hydrocarbyl portion of the aryloxy moiety of the 2-aryloxynaphthalene contains 6 to about twenty carbon atoms. For example, the hydrocarbyl portion can be methyl, ethyl, isopropyl, phenyl, tolyl, etc. When a 2-alkoxynaphthalene is transethylated according to the method of this invention, a 2-alkoxy-6-ethylnaphthalene is produced. When a 2-aryloxynaphthalene is transethylated according to the method of this invention, a 2-aryloxy-6-ethylnaphthalene is produced. The most preferred feed compound for the method of this invention is 2-methoxynaphthalene and the most preferred product is 2-methoxy-6-ethylnaphthalene. The structure of 2-methoxy-6-ethylnaphthalene is as follows:

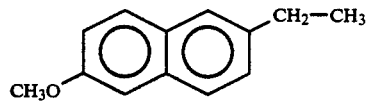

The polyethylbenzene ethylating agents suitable for use in the method of this invention include the triethylbenzenes, tetraethylbenzenes and pentaethylbenzene. From among the polyethylbenzene ethylating agents suitable in the method of this invention, those that have ethyl groups positioned para to each other are the most preferred. Thus, 1,2,4-triethylbenzene, any tetraethylbenzene, pentaethylbenzene, and mixtures thereof are the preferred ethylating agents. Since all tetraethylbenzenes have at least one pair of ethyl substituents in ring positions that are located para to each other, all tetraethylbenzenes are highly suitable ethylating agents. Hexaethylbenzene forms an irreversible addition complex with the acid catalyst and, therefore, is not an effective ethylating agent. Most preferably a tetraethylbenzene, and particularly 1,2,4,5-tetraethylbenzene, is the ethylating agent in the method of this invention. Although the hereinabove described polyethylbenzene ethylating agents are the preferred ethylating agents for the method of this invention, other ethylating agents are also suitable, such as polyethylbenzenoid compounds having no more than five ethyl groups per benzene ring. For example, the di-, tri- and tetraethyltoluenes, the di- and triethylxylenes, i.e. di- and triethyl-o-xylenes, m-xylenes and p-xylenes, tri-, tetra- and pentaethylphenol, polyethylated biphenyls and the like, are polyethylbenzenoid compounds having no more than five ethyl groups per benzene ring and are suitable ethylating agents in the method of this invention. Preferably, the hereinabove described polyethylbenzenoid compounds have at least three ethyl groups per benzene ring. The mole ratio of the ethylating agent to 2-alkoxy- or 2-aryloxy-feed compound is in the range of from about 0.5:1, preferably from about 1:1, to about 10:1, preferably to about 5:1, in the method of this invention. Most preferably, the mole ratio of ethylating agent to 2-alkoxy-or 2-aryloxy-feed compound is in the range of about 2:1 to about 5:1.

As described hereinabove, the ethylating agent used in the transethylation reaction of this invention can be a triethylbenzene, any tetraethylbenzene, pentaethylbenzene, or mixtures thereof. It is most convenient, however, to use a mixture of these polyethylated benzene compounds as the ethylating agent. A mixture is easily prepared and a separation step is avoided. The mixture of polyethylated benzenes is suitably prepared by ethylating benzene or, preferably, a partially ethylated benzene compound such as ethylbenzene, diethylbenzene or triethylbenzene. Benzene or the partially ethylated benzene compound is suitably ethylated with ethylene in the liquid phase in the presence of a Lewis acid catalyst and, preferably, a promoter such as hydrogen chloride, hydrogen bromide, ethyl bromide or chloride. The ethylene is added until the desired mixture of polyethylated benzene compounds is produced. The temperature for the ethylation is suitably in the range of 30° C. to about 100° C. It is most desirable to continue the ethylation until the concentration of tetraethylbenzene is maximized. For example, a suitable mixture of polyethylated benzenes contains about 20 weight percent triethylbenzene, about 70 weight percent tetraethylbenzene and about 5 weight percent pentaethylbenzene. The polyethylated benzene mixture is preferably at least 70 weight percent tetra- and pentaethylbenzene, and it is most preferred for the tetraethylbenzenes to be at least 50 weight percent of the polyethylated benzene mixture. It is to be understood that the hereinabove described polyethylbenzene compounds can be made by other methods and still be useful in the method of this invention.

The transethylation reaction of the present invention is conducted in the liquid phase in the presence or absence of a solvent. Any liquid that is inert under the reaction conditions employed and serves as an effective solvent for the organic reactants and products is suitable. Suitable solvents include halocarbons, such as methylene chloride, chlorobenzene, 1,1-dichloroethane, 1,2-dichloroethane, and chloroform, or carbon disulfide, benzene, cyclohexane, and n-octane. Solvents which are basic and bind irreversibly with the catalyst are not suitable. Such unsuitable solvents include ketones, aldehydes, esters, ethers, and alcohols. Preferably, the solvent, if used, is methylene chloride. If a solvent is employed, the weight ratio of solvent-to-feed compound is in the range of from about 1:1, preferably from about 2:1, to about 15:1, preferably to about 8:1.

Lewis acids and Bronsted acids or mixtures thereof that are conventionally used as alkylation catalysts are suitable for use as the catalyst in the method of this invention. Suitable acid catalysts include aluminum chloride, aluminum bromide, tantalum pentachloride, antimony chloride, antimony pentafluoride, boron trichloride, boron trifluoride, ferric bromide, ferric chloride, sulfonated zirconia, trifluoromethanesulfonic acid, titanium chloride, tin chloride, zirconium tetrachloride, and "red oil," a complex polar liquid phase catalyst which is synthesized for example by the addition of ethyl chloride or bromide, or hydrogen chloride or bromide, to a slurry of aluminum chloride or some other suitable Lewis acid in an aromatic solvent such as benzene, methylbenzene, ethylbenzene, mixed dimethylbenzenes, mixed diethylbenzenes, mixed tetraethylbenzenes or mixed polyethylated benzenes, and which forms a separate liquid phase below the phase containing the feed. Preferably, aluminum chloride or red oil containing aluminum chloride is the catalyst.

The catalyst can be employed as a separate immiscible layer such as the aforementioned red oil, or it can be dissolved with the reactants and products in an organic solvent such as methylene chloride or chlorobenzene. Thus, depending upon the selection of solvent for the catalyst, the feed, ethylating agent and catalyst can be present in a single liquid phase, or the feed and catalyst can be present in separate liquid phases. In the alternative, the catalyst can be in the form of a solid, for example, aluminum chloride deposited or intercalated with graphite, a zeolite or $BF_3$ treated alumina. The catalyst in the method of this invention is typically employed at a level in the range of from about 0.01, preferably from about 0.1, to about 1.0, preferably to about 0.5 mole per mole of 2-alkoxy- or 2-aryloxynaphthalene feed compound.

If the reaction is performed continuously or batchwise, the residence time is from 0.1, preferably from about 1, to about 25, preferably to about 5 hours. However, longer reaction times can be used, particularly when using low reaction temperatures and low levels of catalyst. The reaction temperature for the transethylation reaction is in the range of about $-10°$ C., preferably from about 20° C. to about 100° C., preferably to about 80° C. Most preferably, the reaction temperature is from about 40° C. to about 80° C., particularly for the ethylation of 2-methoxynaphthalene. The reaction pressure must be sufficiently high to maintain the reactants and products in the liquid phase at the particular reaction temperature employed and generally is in the range of from about 0.5, preferably from about 0.8, to about 10, preferably to about 5, atmospheres absolute.

Preferably, and particularly when a polar solvent is not used, a hydrogen halide, such as hydrogen chloride, or an alkyl, alkylene or alkylidene halide is employed as a promoter in the method of the present invention. Typically, such alkyl, alkylene, or alkylidene halides include a methyl halide, such as methyl chloride, or a methylene, ethylene, or ethylidene halide. The promoter is employed at a level of from about 0.1, preferably from about 0.5, up to about 100, preferably up to at least about 2 moles per mole of catalyst (for red oil, based on the aluminum chloride content of the red oil). When a solvent such as an alkyl or alkylene halide is used, it also serves as a promoter.

The 2-methoxynaphthalene useful as a feed for the method of this invention can be prepared by methylating 2-naphthol by any one of a number of techniques known in the art such as, for example, the reaction of the alkali or other metal salt of 2-naphthol with a methylating agent such as methyl iodide or dimethyl sulfate and using a suitable solvent. Alternatively 2-methoxynaphthalene can be purchased from, for example, the Aldrich Chemical Company, Milwaukee, Wis.

The 2-alkoxy- or 2-aryloxy-6-ethylnaphthalene, and particularly the 2-methoxy-6-ethylnaphthalene prepared by the method of this invention, is suitably isolated from the reaction mixture by first quenching the alkylation catalyst with, for example, water, optionally containing a caustic component, or with an alcohol such as methanol. Optionally, the catalyst or catalyst layer is first separated from the reaction mixture and recycled for use in subsequent reactions. However, for the ethylation of 2-methoxynaphthalene using aluminum chloride as the catalyst we found that the catalyst layer incorporates a substantial portion of the desired 2-methoxy-6-ethylnaphthalene product and, consequently, it is desirable to quench the catalyst layer in order to recover the 2-methoxy-6-ethylnaphthalene contained therein.

After the reaction mixture is quenched it is optionally dried to remove any water. The reaction product is then typically subjected to a distillation procedure, preferably fractional distillation, to isolate the desired product-containing fraction. Unreacted feed material and unreacted ethylating agent can be recycled. For example, recovered ethylbenzene, diethylbenzenes and triethylbenzenes can be re-ethylated to form tetra- and pentaethylbenzene. The product-containing fraction may contain other isomers in addition to the desired 2,6-isomer. For example, the distillation of the product produced by the ethylation of 2-methoxynaphthalene according to the method of this invention produces a product fraction containing a major amount of 2-methoxy-6-ethylnaphthalene and minor amounts of 2-methoxy-3-ethylnaphthalene and methoxydiethylnaphthalenes.

The desired 2,6-isomer in the product-containing fraction, e.g., 2-methoxy-6-ethylnaphthalene, can be isolated in pure form using a recrystallization procedure. Low molecular weight monohydroxylic alcohols having 1-6 carbon atoms, and preferably methanol, ethanol or isopropanol, were found to be suitable recrystallization solvents. Methanol is the most preferred recrystallization solvent. Recrystallization from a low molecular weight alcohol such as methanol provides for the desired 2,6-isomer in pure form, for example, a purity of about 99.5% or greater can be achieved.

In the recrystallization method of this invention, the weight ratio of monohydroxylic alcohol to product-containing distillation fraction is preferably in the range of about 5:1 to about 0.5:1 and more preferably about 3:1 to about 1:1, by weight. The recrystallized 2-alkoxy- or 2-aryloxy-6-ethylnaphthalene compound, and particularly 2-methoxy-6-ethylnaphthalene, is readily isolated by filtration, centrifugation, etc. An optional washing step, typically with chilled solvent, can be used.

The 2-methoxy-6-ethylnaphthalene produced by the transethylation of 2-methoxynaphthalene according to the method of this invention is useful for preparing 2-(6-methoxy-2-naphthyl) propionic acid. For example, 2-methoxy-6-ethylnaphthalene can be dehydrogenated to prepare 2-methoxy-6-vinylnaphthalene which, in turn, can be carboxylated by one or more methods known in the art to form 2-(6-methoxy-2-naphthyl) propionic acid. Any means for dehydrogenating 2-methoxy-6-ethylnaphthalene to 2-methoxy-6-vinylnaphthalene is suitable for preparing 2-(6-methoxy-2-naphthyl) propionic acid. Methods for dehydrogenating ethyl substituted aromatic compounds are disclosed, for example, in the Kirk-Othmer Encyclopedia of Chemical Technology, Third Edition, Volume 21, pages 779–785. However, in a preferred method for this dehydrogenation reaction, 2-methoxy-6-ethylnaphthalene is brominated to form the brominated intermediate, 2-methoxy-6-(1-bromoethyl) naphthalene. The bromination is most suitably accomplished by reacting 2-methoxy-6-ethylnaphthalene with N-bromosuccinimide in a non-polar solvent such as carbon tetrachloride. This brominated intermediate is subsequently either thermally or catalytically dehydrobrominated to produce the vinyl compound, 2-methoxy-6-vinylnaphthalene. The dehydrobromination can suitably be conducted by reacting the isolated brominated intermediate with a base catalyst. Methods for conducting dehydrohalogenation reactions are disclosed in R. C. Larock, Comprehensive Organic Transformations, 1989, pages 131–132, and the references cited therein.

Most preferably, however, the dehydrobromination is conducted at an elevated temperature by heating 2-methoxy-6-(1-bromoethyl) naphthalene in the presence of an aromatic amine such as pyridine. In order to complete the dehydrobromination at a suitable rate, the reaction temperature should be at least about 120° C., and preferably at least about 140° C. When using an aromatic amine such as pyridine, high temperatures can be achieved by conducting the reaction at pressures greater than atmospheric. Alternatively, elevated reaction temperatures can be achieved by using aromatic amines that have a normal boiling point higher than the normal boiling point of pyridine. For example, one or more dimethylpyridines (e.g. 2,6-lutidine), 2,6-diphenylpyridine or 2,4,6-trimethylpyridine are suitable aromatic amines for conducting the dehydrobromination at atmospheric pressure, although higher or lower pressures can be used with these and similar high boiling point aromatic amines.

2-Methoxy-6-vinylnaphthalene can be converted to 2-(6-methoxy-2-naphthyl) propionic acid. Any means for converting 2-methoxy-6-vinylnaphthalene to 2-(6-methoxy-2-naphthyl) propionic acid is suitable for the method of this invention. One method for such conversion utilizes the reaction of carbon monoxide with 2-methoxy-6-vinylnaphthalene, either catalyzed by a transition metal catalyst such as cobalt, nickel, palladium or rhodium, or strong acid, or both. Depending on the reaction conditions, the product from the addition of carbon monoxide to the vinyl group results in either the carboxylic acid, 2-(6-methoxy-2-naphthyl) propionic acid directly, an ester of 2-(6-methoxy-2-naphthyl) propionic acid, or the corresponding aldehyde. The aldehyde can readily be converted to the desired carboxylic acid by a suitable oxidation reaction, such as the reaction with acidic permanganate, chromic acid, bromine or molecular oxygen. Processes for converting olefins to carboxylic acids or aldehydes by reaction with carbon monoxide or an equivalent of carbon monoxide such as formic acid are disclosed, for example, in J. March, Advanced Organic Chemistry, Third Edition, pages 720–723, and the references cited therein. Specific methods for converting 2-methoxy-6-vinylnaphthalene to 2-(6-methoxy-2-naphthyl) propionic acid (or an ester thereof) are disclosed in Takeda, et. al., Ger. Offen. 2,646,792 and Alper, et. al., J. Amer. Chem. Soc. 1990, 112, pages 2803–2804. Unless measures are taken to induce optical activity during the reaction of carbon monoxide with 2-methoxy-6-vinylnaphthalene, a racemic mixture will result. However, separation of d-2-(6-methoxy-2-naphthyl) propionic acid from, for example, the racemic mixture of acids provides for the preparation of Naproxen.

Therefore, the present invention is also a new method for preparing 2-(6-methoxy-2-naphthyl) propionic acid, which process comprises dehydrogenating 2-methoxy-6-ethylnaphthalene to form 2-methoxy-6-vinylnaphthalene, and carboxylating the 2-methoxy-6-vinylnaphthalene. The preferred method for dehydrogenating the 2-methoxy-6-ethylnaphthalene comprises brominating the 2-methoxy-6-ethylnaphthalene, preferably with N-bromosuccinimide in a non-polar solvent such as carbon tetrachloride, followed by dehydrobromination to form 2-methoxy-6-vinylnaphthalene.

Other methods for converting 2-methoxy-6-ethylnaphthalene—now readily available by the method of this invention—to 2-(6-methoxy-2-naphthyl) propionic acid are possible. For example, 2-methoxy-6-(1-haloethyl) naphthalene prepared by halogenating 2-methoxy-6-ethylnaphthalene can be converted to 2-(6-methoxy-2-naphthyl) propionic acid by reacting 2-methoxy-6-(1-haloethyl) naphthalene with magnesium to form a Grignard reagent and then reacting the Grignard reagent with, for example, carbon dioxide to form 2-(6-methoxy-2-naphthyl) propionic acid. A process for preparing such a Grignard reagent is disclosed in U.S. Pat. No. 3,651,106 to Harrison. Other methods for converting an alkyl halide such as 2-methoxy-6-(1-haloethyl) naphthalene to the corresponding carboxylic acid or ester are disclosed in J. March, Advanced Organic Chemistry, Third Edition, pages 431–433, and the references cited therein, and in H. O. House, Modern Synthetic Reactions, Second Edition, pages 808–809, and the referenced cited therein. Additionally, the reaction of 2-methoxy-6-(1-haloethyl) naphthalene with cyanide salts such an alkali cyanide can be utilized to form the corresponding cyano compound by displacement of the halogen. The cyano group can be hydrolyzed to the desired carboxylic acid. Such a process is disclosed in Svoboda, et. al., Cesk. Farm. 1986, Vol. 35, pages 74–76. General methods for preparing benzylic halo compounds are disclosed in R. C. Larock, Comprehensive Organic Transformations, 1989, page 313, and the references cited therein. Therefore, the 2-methoxy-6-ethylnapthalene prepared by the method of this invention is a highly versatile and useful intermediate for preparing 2-(6-methoxy-2-naphthyl) propionic acid.

The following examples are intended to illustrate some of the embodiments of the present invention, but are not intended to limit the scope thereof.

EXAMPLE 1

The following is a procedure for preparing 2-methoxy-6-ethylnaphthalene by the transethylation of 2-methoxynaphthalene.

To a 250 ml., 3-neck, round-bottom flask equipped with a magnetic stirrer and a sparge tube were added 70 g of mixed diethylbenzenes obtained from the Aldrich Chemical Company, Milwaukee, Wis. After cooling the reaction mixture with an ice bath, hydrogen chloride gas was added for three minutes and thereupon 14.48 grams of aluminum chloride were slowly added. Hydrogen chloride gas was again added for three minutes. The reaction flask was then placed in a hot water bath to raise the temperature of the reaction mixture to 85°–90° C. At this point ethylene gas was sparged into the reaction mixture until the level of tetraethylbenzene in the reaction mixture was maximized. The composition of the mixture was monitored by gas chromatography. After the ethylene addition was stopped, the reaction mixture was stirred for an additional 30 minutes at 90° C.

To the above reaction mixture at 15° C. was added a mixture of 29.02 grams of 2-methoxynaphthalene dissolved in 50 ml of dichloromethane. The reaction mixture was permitted to warm to room temperature and after 900 minutes it was heated to 32° C. using a water bath. After 15 hours total reaction time the yield of 2-methoxy-6-ethylnaphthalene was 71.5% as measured by gas chromatography.

This example shows the high yield of 2-methoxy-6-ethylnaphthalene that can be achieved by the method of this invention.

EXAMPLE 2

A polyethylbenzene mixture suitable for ethylating 2-methoxy-naphthalene was prepared as follows: To a 12 liter flask fitted with a nitrogen purge, stirrer and sparge tube was charged 3634 grams of 95% mixed diethylbenzenes (from Aldrich Chemical Company, Milwaukee, Wis.) and 540 grams of anhydrous aluminum chloride. Into this mixture was sparged anhydrous hydrogen chloride until the mixture was saturated with hydrogen chloride. During this addition of hydrogen chloride the temperature of the mixture increased to about 38° C. This reaction mixture was then sparged with ethylene until the amount of tetraethylbenzene in the reaction mixture reached about 58–60 weight percent. During this period the temperature of the reaction mixture increased to about 85° C. and it was maintained at this temperature during the addition of the ethylene using a water bath. After the addition of ethylene the mixture was maintained at approximately 90° C. for one hour. When the stirrer was stopped the product mixture formed a lower, "red oil" layer weighing 1371 grams and an upper, polyethylbenzene layer weighing 4197 grams. Analysis by gas chromatography indicated that the polyethylbenzene layer was 0.2 weight percent diethylbenzene (DEB), 22.0 weight percent triethylbenzene (TrEB), 73.2 weight percent tetraethylbenzenes (TeEB) and 4.6 weight percent pentaethylbenzene (PEB). This mixture of polyethylbenzene was used in the ethylation reactions described below in Examples 3–6.

EXAMPLE 3

2-Methoxynaphthalene was ethylated using the mixture of polyethylbenzene prepared according to Example 2. The reaction was conducted in a 500 ml flask equipped with a stirrer and nitrogen gas inlet tube. The flask was charged with 250 grams of the polyethylbenzene mixture (183 grams of tetraethylbenzene) and 25.7 grams of anhydrous aluminum chloride, and the mixture was sparged with gaseous hydrogen chloride. To this mixture, with stirring, was added 76 grams of 2-methyoxynaphthalene. The temperature was maintained at 40° C. The reaction mixture was sparged at 1 hour intervals with hydrogen chloride. At the end of the reaction the reaction mixture was quenched with water and the product layer analyzed by gas chromatography using a 12.5 meter capillary chromatography column having a crosslinked dimethylsilicone stationary phase. By-products were identified using gas chromatography/mass spectroscopy. When the stirring was stopped either during or at the end of the reaction, the reaction mixture separated into an upper, organic layer and a lower, catalyst-containing layer.

The results are reported in Table I. In this table, and in the following tables, "2-MON" is 2-methoxynaphthalene, "N" is naphthol, "2,6-EMON" is 2-methoxy-6-ethylnaphthalene, "2,3-EMON" is 2-methoxy-3-ethylnaphthene, "EN" is ethylnaphthol, "MEMON" is methylethylmethoxynaphthalene, "DEMON" is diethylmethoxynaphthalene and "CD" is a by-product mixture believed to be mainly the product formed by the condensation of a polyethylbenzene, particularly a tetraethylbenzene, with 2-methoxynaphthalene. The reported conversion (Conver.) is the weight percent 2-methoxynaphthalene consumed. The "Selectivity" is the weight percent of the 2-methoxynaphthalene consumed that is converted to the listed products.

TABLE I

| | | | Reaction Temperature: 40° C. Molar Feed Ratio: TeEB/2-MON/AlCl$_3$ = 2/1/0.4 | | | | | |
|---|---|---|---|---|---|---|---|---|
| Reaction Time (Hrs.) | 2-MON[a] Conver. % | | | Selectivity[a] % | | | | |
| | | N | 2,6-EMON | 2,3-EMON | EN | MEMON | DEMON | CD |
| 10.1 | 13.1 | 14.8 | 67.4 | 6.2 | 0.3 | 1.0 | 0.5 | 9.8 |
| 13.7 | 36.3 | 6.0 | 73.3 | 5.3 | 0.9 | 0.7 | 2.2 | 11.7 |
| 17.5 | 58.7 | 3.4 | 73.4 | 5.0 | 1.3 | 0.5 | 5.6 | 10.7 |
| 17.5[b] | 65.6 | 3.0 | 72.4 | 4.9 | 1.4 | 0.5 | 7.6 | 10.3 |
| 20.7 | 77.5 | 2.3 | 67.7 | 4.8 | 1.6 | 0.4 | 13.0 | 10.0 |

[a]Analysis of organic (top) layer, except where noted.
[b]Analysis of the reaction mixture after it was allowed to remain overnight at room temperature without stirring. Under these conditions there was a phase separation with the lower layer "red oil" containing the catalyst. The reaction rate was very low under these conditions.

EXAMPLE 4

The procedure of Example 3 was repeated except the reaction temperature was 80° C. The results are reported in Table II.

A comparison of the data in Table I with the data in Table II demonstrates that at a temperature of 40° C. the reaction time is longer but a higher selectivity to 2-methyoxy-6-ethylnaphthalene (2,6-EMON) is obtained at equivalent conversion of 2-MON.

TABLE II

| | | | Reaction Temperature: 80° C. Molar Feed Ratio: TeEB/2-MON/AlCl$_3$ = 2/1/0.4 | | | | | |
|---|---|---|---|---|---|---|---|---|
| Reaction Time (Hrs.) | 2-MON[a] Conver. % | | | Selectivity[a] % | | | | |
| | | N | 2,6-EMON | 2,3-EMON | EN | MEMON | DEMON | CD |
| 0.3 | 15.6 | 23.1 | 60.6 | 6.3 | 2.0 | 1.9 | 0.6 | 5.5 |
| 0.6 | 30.7 | 15.3 | 67.4 | 6.0 | 2.9 | 1.1 | 2.0 | 5.1 |
| 0.9 | 42.2 | 12.5 | 67.4 | 5.7 | 3.8 | 1.2 | 3.7 | 5.7 |
| 1.1 | 55.5 | 10.4 | 66.3 | 5.3 | 4.7 | 1.2 | 6.3 | 5.8 |
| 1.4 | 63.1 | 9.1 | 65.3 | 5.1 | 5.0 | 1.3 | 8.4 | 5.9 |
| 1.6 | 71.0 | 8.4 | 62.5 | 4.7 | 6.1 | 1.3 | 11.1 | 5.8 |
| 1.6[b] | 79.9 | 6.8 | 59.4 | 4.5 | 5.6 | 1.6 | 15.6 | 6.3 |
| 1.6[c] | 84.6 | 5.9 | 51.3 | 4.2 | 8.9 | 1.5 | 18.9 | 9.3 |

[a]Analysis of organic (top) layer, except where noted.
[b]Analysis of the reaction mixture after it was allowed to remain overnight at room temperature without stirring. Under these conditions there was a phase separation with the lower layer "red oil" containing the catalyst. The reaction rate was very low under these conditions.
[c]Analysis of the combined upper and lower layers.

EXAMPLE 5

Table III provides the data derived from a series of reactions conducted similarly to that described in Examples 3 and 4 except that the amount of aluminum chloride catalyst was varied from 0.1 to 0.4 moles per mole of 2-methoxynaphthalene. The reaction temperature was 80° C.

The data in Table III demonstrate that reduced catalyst loading increases the time required to achieve 50% conversion. At a ratio of 0.1 moles of catalyst per mole of 2-methoxynaphthalene, a conversion of only 33% was achieved after 40 hours reaction time. Preferable reaction rates were achieved when the mole ratio of catalyst to 2-methoxynaphthalene was in the range of 0.2 to 0.4.

TABLE III

| Molar Feed Ratio (TeEB/2-MON/AlCl$_3$) | Reaction Time (hrs.) | 2-MON Conversion | 2,6-EMON Selectivity (%) |
|---|---|---|---|
| 2/1/0.4 | 1.1 | 55.5 | 66.3 |
| 2/1/0.2 | 2.0 | 50.6 | 66.0 |
| 2/1/0.1 | 40.2 | 32.6 | 57.0 |

EXAMPLE 6

Table IV provides the data derived from a series of reactions conducted similarly to that described in Examples 3 and 4 except the amount of tetraethylbenzene ethylating agent was varied from 0.5 mole to 4.0 moles per mole of 2-methoxynaphthalene. The reaction temperature was 60° C.

These data demonstrate that higher ratios of ethylating agent (i.e., tetraethylbenzene) to 2-methoxynaphthalene result in improved selectivity to 2-methoxy-6-ethylnaphthalene (2,6-EMON).

TABLE IV

| Molar Feed Ratio (TeEB/2-MON/AlCl$_3$) | Selectivity$^a$ % | | | | |
|---|---|---|---|---|---|
| | 2,6-EMON | 2,3-EMON | N | DEMON | CD |
| 0.5/1/0.2 | 56.5 | 8.2 | 3.4 | 5.6 | 26.2 |
| 1/1/0.2 | 66.2 | 6.7 | 5.7 | 7.9 | 13.5 |
| 2/1/0.2 | 70.3 | 5.9 | 7.4 | 6.6 | 9.6 |
| 4/1/0.2 | 74.1 | 5.0 | 4.5 | 8.3 | 8.1 |

$^a$These data are at a 2-MON conversion of about 50%.

EXAMPLE 7

Table V provides data from two reactions conducted similarly to that described in Example 3 except that for the reaction designated A in Table V the ethylating agent was a mixture of 6.7% diethylbenzenes, 89.6% triethylbenzenes, and 0.9% (by weight) tetraethylbenzenes. An amount of this mixture was used so that the mole ratio of triethylbenzenes: 2-methoxynaphthalene: aluminum chloride in the reaction mixture was 1:1:0.2, respectively. For the reaction designated as B in Table V, the ethylating agent was a mixture of 0.1% diethylbenzenes, 3.3% triethylbenzenes, 62.39% tetraethylbenzenes, 33.1% pentaethylbenzenes and 1.2% hexaethylbenzene. An amount of this mixture was added to reaction mixture B so that the mole ratio of tetraethylbenzene: 2-methoxynaphthalene: aluminum chloride was 1:1:0.2, respectively. The reaction temperature for both the A and B reactions was 60° C.

The data in Table V demonstrate that tetraethylbenzene is a superior ethylating agent compared to triethylbenzene. Reaction rate was greater and selectively to the 2-methoxy-6-ethylnaphthalene was greater using tetraethylbenzene as the ethylating agent.

TABLE V

| Reaction | Time (Hrs) | 2-MON Conver. | Selectivity % | | | | | | |
|---|---|---|---|---|---|---|---|---|---|
| | | | N | 2,6-EMON | 2,3-EMON | EN | MEMON | DEMON | CD |
| A | 18 | 26.2 | 15.6 | 37.2 | 4.4 | 1.7 | 0.7 | 0.9 | 39.5 |
| B | 12.8 | 64.8 | 1.6 | 65.4 | 7.0 | 1.9 | 1.0 | 10.7 | 11.6 |

EXAMPLE 8

Large-scale samples of 2-methoxy-6-ethylnaphthalene were prepared according to the following general procedure.

A mixture of diethylbenzenes (3628 grams) was ethylated as in Example 2 using 542.1 grams of anhydrous aluminum chloride as the catalyst. After the addition of ethylene for 295 minutes, followed by a heat soak at 84°-95° C. for 161 minutes, the mixture contained (by weight) 0.36% diethylbenzene, 29.28% triethylbenzenes, 65.35% tetraethylbenzes and 3.16% pentaethylbenzene. To this mixture was slowly added 1424.5 grams of 2-methoxynaphthalene and the resulting reaction mixture was maintained at 36°-41° C. for a total of approximately 25 hours, with stirring. When the stirring was discontinued, the reaction mixture separated into an upper, organic layer and a lower, catalyst-containing "red oil" layer. Both layers were carefully treated first with methanol and then with water to quench the catalyst. The product from the upper layer weighed 4537.2 grams and the product from the lower layer weighed 1641.0 grams. Table VI provides the results of the gas chromatographic analysis of the upper and lower layers.

TABLE VI

| Component | Weight Percent | |
|---|---|---|
| | Upper Layer | Lower Layer |
| ethylbenzene | 0.05 | 0.06 |
| diethylbenzenes | 3.25 | 6.40 |
| triethylbenzenes | 44.81 | 30.46 |
| tetraethylbenzenes | 35.79 | 12.96 |
| pentaethylbenzenes | 2.04 | 0.49 |
| hexaethylbenzenes | 0.00 | 0.00 |
| 2-methoxynaphthalene | 1.21 | 2.76 |
| 2-methoxy-6-ethylnaphthalene | 5.97 | 15.20 |
| 2-methoxy-3-ethylnaphthalene | 0.48 | 2.36 |
| other methoxyethylnaphthalenes | 0.32 | 0.74 |
| diethylmethoxynaphthalene | 2.79 | 15.75 |
| triethylmethoxynaphthalene | 0.15 | 2.41 |
| unknowns | 3.15 | 10.39 |

The product mixture prepared as described above, as well as similarly prepared mixtures, was subjected to a purification procedure in order to isolate pure 2-methoxy-6-ethylnaphthalene. This purification procedure utilized a distillation step to recover a fraction enriched in 2-methoxy-6-ethylnaphthalene followed by a recrystallization step to isolate 2-methoxy-6-ethylnaphthalene in greater than 98% purity. However, prior to the fractional distillation, the reaction mixture was flash distilled to remove most of the lower boiling components such as ethylbenzene, the diethylbenzenes and the triethylbenzenes. A typical fractional distillation of the higher boiling components that remained after the flash distillation was conducted as follows:

A 1292.5 gram sample of the product mixture was fractionally distilled using a 20 tray, 1 inch I.D. Oldershaw fractionation column. The column was silvered and vacuum-jacketed, and a simple distillation head was used to remove fractions. The column was operated at 1.2-1.4 mm/Hg vacuum, and the distillation pot temperature ranged from 176° C. to 250° C. Fractions taken at an overhead temperature of 132° C. to 143° C. contained 56.4 to 91.6 weight percent 2-methoxy-6-ethylnaphthalene. Similar distillations, however, using a 1 inch I.D. silvered, vacuum-jacketed column packed with 16 inches of ProPak ® stainless steel packing, and equipped with swinging-funnel splitter so that a reflux ratio of between 8:1 to 16:1 could be used, provided for a consistently better separation of the desired 2-methoxy-6-ethylnaphthalene from the other products.

A 20.1 gram sample of distillate (40.0 gram fraction at 138° C. overhead) having the composition shown in Table VII was recrystallized from 41.3 grams of methanol followed by a washing with 40 grams of chilled methanol. The composition of the recrystallized product (9.5 grams) is also reported in Table VII. Similar recrystallizations using distillation fractions that contained a higher percentage of 2-methoxy-6-ethylnaphthalene, for example 89 to 94% 2-methoxy-6-ethylnaphthalene, produced 2-methoxy-6-ethylnaphthalene with a purity greater than 99%.

TABLE VII

| Component | Weight Percent | |
|---|---|---|
| | Distillation Fraction | Recrystallized Product |
| 2-methoxynaphthalene | 0.0 | 0.0 |
| 2-methoxy-6-ethylnaphthalene | 66.89 | 98.35 |
| 2-methoxy-3-ethylnaphthalene | 2.13 | 0.0 |
| other methoxyethylnaphthalenes | 0.28 | 0.0 |
| diethylmethoxynaphthalene | 24.06 | 0.38 |
| triethylmethoxynaphthalene | 0.08 | 0.0 |
| unknowns | 6.57 | 1.28 |

This example demonstrates that the recrystallization of the distillation fractions containing 2-methoxy-6-ethylnaphthalene from methanol results in highly pure 2-methoxy-6-ethylnaphthalene.

EXAMPLE 9

Preparation of 2-Methoxy-6-(1-Bromoethyl) Naphthalene: A mixture of 1.0 gram of 2-methoxy-6-ethylnaphthalene and 1.05 grams of N-bromosuccinimide in 10.0 ml. of carbon tetrachloride was refluxed for 1 hour. During this time, the solids migrated from the bottom of the reaction flask to the top. The mixture was cooled to room temperature and the solids were separated from the liquid by filtration on a small suction filter funnel. The carbon tetrachloride solvent was removed using a rotary vacuum evaporator. The yield was 1.55 grams of a pale oil that solidified at room temperature. Based on $^1$H nuclear magnetic resonance data, the product had a structure consistent with that of 2-methoxy-6-(1-bromoethyl) naphthalene.

EXAMPLE 10

Preparation of 2-Methoxy-6-Vinylnaphthalene: The 2-methoxy-6-(1-bromoethyl) naphthalene prepared in Example 9 was dissolved in 8.0 grams of collidine (2,4,6-trimethylpyridine) and the mixture was refluxed for 45 minutes. The product mixture was cooled, diluted with diethylether, and washed with dilute hydrochloric acid. The ether solution was dried over anhydrous magnesium sulfate, filtered and the diethylether removed by evaporation. The structure of the resulting product was verified as 2-methoxy-6-vinylnaphthalene by $^1$H and $^{13}$C nuclear magnetic resonance spectroscopic analysis.

While only certain embodiments have been set forth, alternative embodiments and various modifications will be apparent from the above description to those skilled in the art. These and other alternatives are considered equivalents and within the spirit and scope of the present invention. The entire specification of U.S. patent application Ser. No. 568,581, filed on Aug. 16, 1990, is hereby specifically incorporated by reference.

Having described the invention, what is claimed is:

1. A method for ethylating a 2-alkoxynaphthalene as a feed compound, comprising reacting the feed compound in the liquid phase with an ethylating agent comprising a triethylbenzene, a tetraethylbenzene, pentaethylbenzene, or a mixture thereof, in an amount of from about 0.5 to about 10 moles of the ethylating agent per mole of the feed, in the presence of a catalyst comprising a Lewis acid or Bronsted acid alkylation catalyst or mixture thereof.

2. The method of claim 1 wherein the ethylating agent comprises a tetraethylbenzene, pentaethylbenzene, or a mixture thereof.

3. The method of claim 2 wherein the ethylating agent comprises a tetraethylbenzene.

4. The method of claim 1 wherein the ethylating agent is in an amount of about 1 to about 5 moles per mole of the feed.

5. The method of claim 1 wherein the reaction is conducted in the presence of a promotor comprising a hydrogen halide or an alkyl, alkylene or alkylidene halide, in an amount of from about 0.1 to about 100 moles per mole of the catalyst.

6. The method of claim 1 wherein the alkylation catalyst comprises a catalyst selected from the group consisting of aluminum chloride, aluminum bromide, tantalum pentachloride, antimony chloride, antimony pentafluoride, boron trichloride, boron trifluoride, ferric chloride, ferric bromide, sulfonated zirconia, trifluoromethanesulfonic acid, red oil, bismuth chloride, tin chloride, titanium chloride, zirconium tetrachloride, zinc chloride, zeolites and $BF_3$-treated alumina.

7. The method of claim 6 wherein the catalyst is aluminum chloride.

8. The method of claim 1 wherein the feed compound is 2-methoxynaphthalene.

9. The method of claim 8 wherein the catalyst is aluminum chloride.

10. The method of claim 8 wherein the ethylating agent comprises tetraethylbenzene in an amount of from about 1 to about 5 moles of tetraethylbenzene per mole of 2-methoxynaphthalene.

11. The method of claim 8 wherein the reaction is conducted at a temperature in the range of about 20° C. to about 80° C.

12. The method of claim 8 wherein 2-methoxy-6-ethylnaphthalene is produced and the 2-methoxy-6-ethylnaphthalene is isolated by distillation followed by recrystallization from a low molecular weight alcohol.

13. The method of claim 8 wherein 2-methoxy-6-ethylnaphthalene is produced and wherein the 2-methoxy-6-ethylnaphthalene is brominated to form 2-methoxy-6-(1-bromoethyl) naphthalene.

14. The method of claim 13 wherein the 2-methoxy-6-(1-bromoethyl) naphthalene is dehydrobrominated to form 2-methoxy-6-vinylnaphthalene.

15. The method of claim 14 wherein said dehydrobromination comprises heating 2-methoxy-6-(1-bromoethyl) naphthalene in the presence of an aromatic amine at a temperature of at least about 120° C.

16. A method for ethylating a 2-alkoxynaphthalene as a feed compound, comprising reacting the feed compound in the liquid phase with a polyethylbenzenoid ethylating agent having no more than five ethyl groups per benzene ring, in an amount of from about 0.5 to about 10 moles of the ethylating agent per mole of the feed, in the presence of a catalyst comprising a Lewis acid or Bronsted acid alkylation catalyst or mixture thereof.

17. The method of claim 16 wherein the feed compound is 2-methoxynaphthalene.

18. The method of claim 16 wherein the acid alkylation catalyst is present in an amount of from 0.01 to about 1 mole of catalyst per mole of feed.

* * * * *